US012453825B2

(12) United States Patent
Gallagher et al.

(10) Patent No.: US 12,453,825 B2
(45) Date of Patent: Oct. 28, 2025

(54) MOUTHPIECE OF PULMONARY DELIVERY DEVICE HAVING WARM AND COLD CHAMBERS

(71) Applicant: TWENTY SIXTEEN (2016) PHARMA LIMITED, Caerwys Clwyd (GB)

(72) Inventors: George Gallagher, Caerwys Clwyd (GB); Anant Pandya, Croydon (GB)

(73) Assignee: Twenty Sixteen (2016) Pharma Limited, Caerwys Clwyd (GB)

( * ) Notice: Subject to any disclaimer, the term of this patent is extended or adjusted under 35 U.S.C. 154(b) by 0 days.

(21) Appl. No.: 18/530,429

(22) Filed: Dec. 6, 2023

(65) Prior Publication Data

US 2024/0100265 A1 Mar. 28, 2024

Related U.S. Application Data

(63) Continuation of application No. 17/980,621, filed on Nov. 4, 2022, now abandoned, which is a
(Continued)

(30) Foreign Application Priority Data

Aug. 9, 2017 (GB) ..................................... 1712749
Sep. 15, 2017 (GB) ..................................... 1714880

(51) Int. Cl.
*A24F 40/30* (2020.01)
*A24F 40/42* (2020.01)
(Continued)

(52) U.S. Cl.
CPC ........... *A61M 11/041* (2013.01); *A24F 40/30* (2020.01); *A24F 40/42* (2020.01); *A24F 40/48* (2020.01);
(Continued)

(58) Field of Classification Search
CPC .......... A24F 40/30; A24F 40/42; A24F 40/48; A24F 40/485
See application file for complete search history.

(56) References Cited

U.S. PATENT DOCUMENTS 7,726,320 B2 * 6/2010 Robinson ................. H05B 3/42 131/194
10,123,568 B1 * 11/2018 Zhu ......................... A24F 40/46
(Continued)

FOREIGN PATENT DOCUMENTS

AU 2013/352004 11/2013
CN 102883767 1/2016
(Continued)

OTHER PUBLICATIONS

PCT International Search Report And Written Opinion, PCT/IB2018/055626, Jan. 21, 2019.
GB Search Report, GB1812265.5, Oct. 26, 2019.

*Primary Examiner* — Hae Moon Hyeon
(74) *Attorney, Agent, or Firm* — Neil D. Gershon

(57) ABSTRACT

A pulmonary delivery device (300) with a first chamber (206) adapted to thermally vaporise a quantity of a first fluid to form a relatively warm first vapour and a second chamber (208) adapted to atomize a quantity of a second fluid without heating of the second fluid to form a mist of a relatively cold, second vapour, the device further comprising an outlet via which, in use, a user can inhale a mixture of the first and second vapours. The second chamber is in the form of a passive atomiser wherein the second chamber is selectively or continuously in fluid communication with air, the second chamber including at least one flavouring or aroma wherein the flavour is inhaled by drawing air through the chamber.

8 Claims, 7 Drawing Sheets

Related U.S. Application Data continuation of application No. 16/636,423, filed as application No. PCT/IB2018/055626 on Jul. 27, 2018, now Pat. No. 11,504,486.

(51) Int. Cl.

| | |
|---|---|
| ***A24F 40/48*** | (2020.01) |
| ***A24F 40/485*** | (2020.01) |
| ***A61M 11/04*** | (2006.01) |
| *A24F 40/05* | (2020.01) |
| *A24F 40/10* | (2020.01) |
| *A24F 40/20* | (2020.01) |
| *A24F 40/46* | (2020.01) |

(52) U.S. Cl.

CPC ............ *A24F 40/485* (2020.01); *A24F 40/05* (2020.01); *A24F 40/10* (2020.01); *A24F 40/20* (2020.01); *A24F 40/46* (2020.01)

(56) References Cited

U.S. PATENT DOCUMENTS

| | | | | |
|---|---|---|---|---|
| 10,645,975 | B2 | 5/2020 | Qiu | |
| 11,504,486 | B2 * | 11/2022 | Gallagher | A61M 11/042 |
| 11,819,055 | B2 * | 11/2023 | Hubbard | A61M 15/06 |
| 2013/0074857 | A1 | 3/2013 | Buchberger | |
| 2014/0144429 | A1 | 5/2014 | Wensley et al. | |
| 2016/0324216 | A1 * | 11/2016 | Li | A24F 40/42 |
| 2016/0331037 | A1 | 11/2016 | Cameron | |
| 2017/0157341 | A1 | 6/2017 | Pandya | |
| 2017/0224014 | A1 | 8/2017 | Fraser | |
| 2017/0238611 | A1 | 8/2017 | Buchberger | |
| 2018/0035719 | A1 * | 2/2018 | Turner | A24F 40/30 |
| 2018/0132534 | A1 * | 5/2018 | Reevell | A24F 40/485 |
| 2018/0325174 | A1 | 11/2018 | Sutton | |
| 2019/0124982 | A1 | 5/2019 | Atkins | |
| 2019/0254343 | A1 * | 8/2019 | Hepworth | A24D 3/061 |

FOREIGN PATENT DOCUMENTS

| | | |
|---|---|---|
| CN | 106535682 | 7/2019 |
| JP | 2016/501588 | 1/2016 |
| WO | WO 2014/187770 | 11/2014 |
| WO | WO 2015/079197 | 6/2015 |
| WO | WO 2016/012774 | 1/2016 |
| WO | WO 2016/179376 | 11/2016 |
| WO | WO 2017/081487 | 5/2017 |
| WO | WO 2017/153592 | 9/2017 |
| WO | WO 2019/012151 | 1/2019 |
| WO | WO 2019/207012 | 10/2019 |

* cited by examiner

MOUTHPIECE OF PULMONARY DELIVERY DEVICE HAVING WARM AND COLD CHAMBERS

CROSS-REFERENCES TO RELATED APPLICATIONS

This application is a continuation of application Ser. No. 17/980,621, filed Nov. 4, 2022, which is a continuation of application Ser. No. 16/636,423, filed Feb. 4, 2020, which is a 371 of PCT/IB2018/055626, filed Jul. 27, 2018, which claims priority from application GB1712749.9, filed Aug. 9, 2017 and application GB1714880.0, filed Sep. 15, 2017. The entire contents of each of these applications are incorporated herein by reference.

TECHNICAL FIELD

This invention relates to pulmonary delivery devices, particularly but not exclusively, to pulmonary delivery devices suitable for delivering active molecules and/or medicaments to users, such as nicotine, cannabinoid, peptides, proteins and other lung deliverable medicaments and other vape products.

Pulmonary delivery devices have widespread uses in modern medicine as they enable drugs and medicaments to be delivered directly to the user's lungs. Moreover, as medicaments delivered to the lungs enter the bloodstream directly, rather than via the body's metabolism, as is the case with oral delivery systems, the benefits of the medicament, especially in pain relief or drug-weaning applications, are felt by the user almost immediately. Another major benefit of pulmonary delivery devices is their ability to deliver drugs without the use of needles.

Existing pulmonary delivery systems take various forms, including inhalator sprays, nebulisers, metered dose inhalers in which the medication is administered in the form of a mist inhaled by the lungs and vapour delivery systems whereby the medicament is admixed to an inhalable vapour (often a water-containing vapour).

A vapour type pulmonary delivery system comprises a carrier liquid, often water or a water-glycol mixture (the glycol serving to stabilise the water droplets when in the vapour form) to which is admixed a desired medicament. The carrier liquid can be vaporised in various ways, such as by spraying it through a nozzle, but in many cases, it is simply heated to form a vapour comprising the carrier liquid and the desired medicament. The resultant vapour is then inhaled by a user to deliver the medicament. However, heating of the medicament can result in undesirable by-products being formed and thus, inhaled by the user. This may also reduce the accuracy of the dose of medicament inhaled.

An example of a vapour type pulmonary delivery system is an e-cigarette that vapes nicotine for inhalation by the user. A nicotine solution ("e-liquid") is provided in a reservoir (often in the form of a detachable cartridge) and passes along a wick to a heating element where it is vaporised and can be inhaled by the user. Generally, a length of resistance wire connected to a power source, such as a battery, is coiled around the wick. When activated the wire heats up, turning the e-liquid to vapour which is then inhaled by the user. Such a device has clear advantages over smoking conventional cigarettes since far fewer, and safer, ingredients are inhaled by the user than when smoking an ordinary tobacco cigarette. However, regular users have noted that the e-cigarettes do not "hit the spot" in the manner of a conventional tobacco cigarette. This is due to the wet vapour quickly condensing in the mouth of the user, resulting in the majority of nicotine absorption being through the mucous membranes of the nose, throat and airway leading to the lungs. In contrast, with conventional cigarette smoking, nicotine passes straight into the lungs giving a rapid absorption into the blood stream and a corresponding "quick hit".

An alternative type of e-cigarette is an atomizer inhaler. This type of device provides a better, more rapid absorption of nicotine due to the use of a cold, pressurized vapour in place of a heated vapour, thereby avoiding significant condensation of the vapour in the mucosa of the nose and throat. However, the cold and dry sensation provided by this type of device results in the overall experience differing greatly to smoking conventional cigarettes resulting in such devices being less popular than the vaping type e-cigarettes, resulting in none or poor compliance.

The Applicant's co-pending PCT Patent Publication No. WO 2015/079197 provides a solution to this problem by the provision of a first chamber having a heat source adapted to thermally vaporise a quantity of a carrier liquid to form a heated first vapour and a second chamber adapted to atomize a quantity of a second liquid containing an active molecule or medicament without heating of the second liquid to form a mist of a second vapour having a lower temperature than the first vapour, and an outlet via which, in use, a user can inhale a mixture of the first and second vapours. In this manner, rapid absorption of an active molecule contained in the second vapour is achieved while providing the user with a desirable heat sensation on inhalation provided by the vapour of the "warm" first liquid.

Electronic nicotine delivery systems (ENDS) are often provided to deliver flavours in conjunction with the vaporised nicotine. However, a problem exists due to the risk of inhalation of the ingredients of the flavourings, such as oils, with some being potentially carcinogenic when vaporised or delivered to the lung. Furthermore, it is difficult to change the flavour of the system without carryover or contamination in the main body of the system. Coffee, tobacco, mint and fruit flavours are often difficult to alternate due to their characteristic aromas. Currently, the flavours form an integral part of the propylene glycol/water carrier liquid which contaminates the main body of the device.

It is an aim of the present invention to provide an improved pulmonary delivery device that overcomes, or at least alleviates, the abovementioned drawbacks.

SUMMARY OF THE INVENTION

Accordingly, the present invention provides a pulmonary delivery device comprising: a first chamber adapted to thermally vaporise a quantity of a first fluid to form a relatively warm, wet first vapour; a second chamber adapted to atomize a quantity of a second fluid without heating of the second fluid to form a mist of a relatively cold, second vapour, and an outlet via which, in use, a user can inhale a mixture of the first and second vapours wherein the second chamber comprises a passive atomiser wherein the second chamber is selectively or continuously in fluid communication with air, the second chamber including at least one flavouring or aroma and optionally an active molecule or medicament wherein the flavour/aroma and optional other active molecule or medicament are inhaled by drawing air through the second chamber.

The flavourings and/or aroma may be selected from essential oils of dried flowers, buds, leaves, stems, fruit, seeds, peel, bark, or root e g oil of peppermint, spearmint, eucalyptus, wintergreen, clove, cardamom, cinnamon, bitter almond, coriander, caraway, ginger, juniper, orange, bitter orange, lemon, grapefruit, bergamot, thyme, fennel rosemary etc., natural flavors and aroma agents of essential oils or concentrates of flavor components with natural origin from e g fruits, berries, nuts, spices, mints, tobacco, cocoa, coffee, tea, vanilla, liquorice, caramel, toffee, honey, wine, liquors and brews, synthetic flavors and aroma agents consisting of mixtures of chemicals comprising hydrocarbons, alcohols, aldehydes, esters, ketones, ethers and oxides blended to match the natural flavor of e g fruits, berries, nuts, spices, mints, tobacco, cocoa, coffee, tea, vanilla, liquorice, caramel, toffee, honey, wine, liquors or brews and mixtures thereof.

Preferably, the first chamber is provided with, or connected to, a heat source for vaporisation of the first fluid thereby creating a first "warm" vapour. Preferably, the active molecule or medicament is included in the second fluid forming a "cold" vapour". In this manner, rapid absorption of an active molecule contained in the second vapour is achieved while providing the user with a desirable heat sensation on inhalation provided by the vapour of the "warm" first fluid. Alternatively, the active molecule or medicament may be included in the first fluid, forming a "hot vapour".

The first fluid may comprise a carrier liquid (i.e. a liquid capable of forming a stable vapour), which may be an inert (non-medicated carrier liquid), such as water, or a water-glycol mixture.

Preferably, the flavour is provided in a solid or semi-solid form within the second chamber in a suitable formulation. Preferably, the volume of air inhaled through the second chamber is selectively adjustable thereby enabling the amount of flavour inhaled to be varied and deposited in the mouth to enhance the flavour and avoid thermal decomposition thus avoiding carcinogenic degradant products.

More preferably still, the device is provided with an outlet in the form of a mouthpiece, preferably being reversibly detachable, from the first and/or second chambers. In this manner, the flavour may be provided in the mouthpiece to enable its easy replacement, for example to change to a different flavour or to allow replenishment of the flavour. The mouthpiece preferably comprises first and second mouthpiece chambers. The flavour, preferably being in solid or semi-solid form, is provided in the second mouthpiece chamber. In a preferred embodiment, the mouthpiece comprises a central first mouthpiece chamber and a concentric outer second mouthpiece chamber, the second chamber having at least one air inlet. Preferably, a flavour block is provided in the second chamber.

It is to be appreciated that the pulmonary delivery device may include only the first chamber with the mouthpiece providing the second chamber, preferably the mouthpiece provides an extension to the first chamber in addition to providing the second chamber that preferably surrounds the extension to the first chamber.

Preferably, the central first chamber of the mouthpiece is dimensioned for receipt within a main first chamber provided in a pulmonary delivery device that produces heated or warm vapour. Suitable attachment means is provided for attachment of the mouthpiece to the main device. For example, the end of the first mouthpiece chamber may be threaded or comprise a snap-fit arrangement. The outer second mouthpiece chamber may terminate in a flange having at least one air inlet wherein the flange is received on a top surface of the main first chamber of the main body of the pulmonary delivery device. Preferably, multiple air inlets are provided at spaced apart intervals, preferably being equidistance apart, at the base of the second chamber. This provides control for optimized airflow for controlled or no flavour delivery.

Alternatively, an annular flange may extend laterally from a region of the first mouthpiece chamber that contacts that the main body of the device, the flange being provided with holes to allow air into the second mouthpiece chamber surrounding the first chamber.

Preferably, the entry of air through the inlets may be controllable and/or variable. For example, the number of air inlets that are open may be adjustable to suit the preference of the user. Any suitable mechanism may be employed to allow opening and closing of one or more of the multiple inlets.

In one embodiment, the mouthpiece may comprise two parts, one part forming the central first chamber, at least a portion of the first chamber including air inlets in fluid communication with a second chamber formed by a second part surrounding the first part. Preferably, the second part is at least partially rotatable with respect to the first part to effect closing or opening of one or multiple air inlets provided in the first part. Alternatively, the first part may be rotatable with respect to the second part.

Alternatively, the mouthpiece may include means for closing a portion of the air inlets simultaneously (such as all air inlets on one half or one quarter of the chamber). In this manner, the mouthpiece may be provided with different flavours in the second chamber and the user may select a flavour according to their preference. For example, two semi-cylinder flavour blocks may be provided in opposing sides of the second mouthpiece chamber and air inlets selectively opened on the side of the chamber that contains the desired flavour.

It is to be appreciated that it is possible to control the composition of the mixture by controlling the quantity of vapour released from one or each of the main chambers or mouthpiece chambers. Suitably, the delivery apparatus may comprise a controller adapted to control, in use, the composition of the first and/or second vapours in the mixture, that is to say, by controlling the relative amounts of the first and second vapours in the mixture, or the ratio between the two. The controller could be adapted to switch one or the other of the vaporisers on or off, thus providing the option of delivering one or the other of the liquids in vapour form.

The first main chamber of the pulmonary delivery device preferably comprises a vaporiser in the form of an electric heater, for example a battery-powered resistive heating wire or coil. The current delivered to the resistive heating wire or coil can be used to control the temperature of the wire or coil, and thus regulate and/or control the heating and vaporisation of the liquids. In an embodiment of the invention, the heater comprises a hydrophilic or super-hydrophilic foil, which coats with a film of the liquid to be vaporised. A current can be passed through the coil to heat it, thereby vaporising the liquid. Alternatively, a ceramic heater may be used as the heat source. The use of a ceramic or other suitable material heater may be preferred as it reduces the potential for metals to be transferred/inhaled into the user's lung i.e. metal elements exposed to the high temperature may result in harmful metal residue being delivered to the lungs.

A feedback circuit may be provided to thermostatically regulate the temperature, or temperature profile of the heater. For example, a circuit may be provided to monitor the resistance of the wire or coil (the resistance being dependent on the wire or coil's temperature) and to adjust the current in the wire or coil such that
the resistance, and hence the temperature, is controlled.

The vaporiser suitable for use in the first chamber of a pulmonary delivery device according to the present invention may comprise an electric heater adapted to vaporise a quantity of vaporisable liquid in contact therewith, the vaporiser further comprising a circuit configured to apply a time-dependent heating and/or cooling profile by temporally controlling an electric current in the heater in response to a measured temperature thereof.

Such a configuration, that is to say, a time-dependent heating and/or cooling profile, suitably controls the vaporisation of the liquid or liquids more precisely and reproducibly, and/or improves the longevity of the heater, which is suitably a heating wire, foil, coil or ceramic tube.

Other heating devices could equally be used, such as thermionic emitters, Peltier devices, infrared emitters and so forth, and the invention is not restricted to resistive heater wires, foils or coils.

The second liquid is vaporised by atomising or forcing a liquid through a nozzle or aperture to form a stable cold vapour or mist. This not only provides the user with rapid absorption of the active molecule but avoids potential degradation of the active ingredient or excipients such as flavours which may expose the user to potential harmful by-products.

Any suitable atomiser may be incorporated into the device for forming the mist of the second vapour, such as an aerosol dispensing system, ultrasonic vibrators, compressors and electrical vibrating mesh technology. Preferably, the particles produced using suitable formulation in the mist provided by the second chamber have an average diameter of 5 to 50 μm, more preferably 8-35 μm. The flavour and/or active molecule is provided in a suitable formulation to provide the desired particle size. For example, a suitable formulation may include viscosity enhancers, surfactants, stabilizers and/or humectants to optimise the organoleptic properties.

By having the flavouring and optionally, the active molecule or medicament in the cold chamber, the dosage of the active can be controlled more accurately with reproducible dosage i.e. by not exposing the active molecule or medicament to high temperature and designing the atomization to be more accurate & reproducible. Additionally, the potentially flavours are not heated to produce harmful by-products (degradants) and do not enter the stomach.

It is to be appreciated that the delivery of the medicament to the lungs of the user may be controlled and/or varied by selection of the particle droplet size and velocity of the second vapour.

In an embodiment of the invention, for example, a nicotine weaning device, the pulmonary delivery system resembles a cigarette, a pipe or a cigar. In such a situation, the first fluid can comprise an inert mixture of water and glycol and the second fluid can contain a mixture of a propellant, flavouring and/or the desired medicament, in this case, liquid nicotine. The device can thus be programmed to deliver a certain dose of medicament (nicotine) in each "puff" of the device, or over a given period, such as a day. However, the nicotine may also be provided in the first fluid, as desired and, indeed, in certain cases, this may be preferred with only the flavouring being contained in the second fluid expelled from the second chamber.

In one embodiment, the vaporiser of the first main chamber of the pulmonary delivery device suitably comprises a reservoir for retaining, in use, a quantity of the respective liquid and a conveyor adapted to convey, in use, the liquid from the reservoir to a heater. In an embodiment of the invention, the reservoir comprises a vial and the conveyor comprises a wick extending between the interior of the vial and the heater. Suitably, a resistive heating wire, such as that described herein, can be wrapped or coiled around the wick to vaporise the liquid. The conveyor may comprise a capillary tube extending between the vial and the heater.

The first and/or second fluids may suitably comprise a solvent and a stabiliser in an appropriately designed formulation/recipe. The stabiliser is suitably adapted to stabilise droplets of the solvent in air. The carrier liquid can comprise any one of more of the group comprising:

- solubilizers, solvents and mixtures thereof such as water, alcohols such as glycerol, propylene glycol, polyethylene glycol, vegetable oils, mineral oils, lipids, cyclodextrins etc. Surface active agents such as anionic agents with carboxylate ions, sulphate groups and sulphonate groups; cationic surfactants, nonionic surfactants such as polyol ethers, polyoxyethylene esters and ethers, poloxamers; amphoteric surfactants, natural emulsifiers, sucrose esters and alkylpolyglucosides;
- antioxidants such as ascorbic acid and its salts and derivatives tocopherols (vitamin E), thiol derivatives such as cysteine and acetyl cysteine, butylated hydroxyanisole (BHA), butylated hydroxytoluene (BHT), sodium hydrogen sulfite, sodium metabisulfite, sodium thiosulfate;
- absorption enhancers such as alcohols, azone;
  - chelating agents, such as Ethylenediaminetetraacetic acid (EDTA) and galates;
- minerals, such as fluorides;
- propellants, such hydrofluoroalkanes (HFA) Chlorofluorocarbons (CFCs), carbon dioxide etc.; sweeteners such as artificial sweeteners e g saccharin and its sodium and calcium salts, aspartame, acesulfame and its potassium salt, thaumatin and glycyrrhizin, polyhydric alcohols such as sorbitol, xylitol, mannitol and glycerol, glucose, fructose, galactose, sucrose, lactose, maltose and mixtures thereof;
- and
- pH regulators and buffering agents such as sodium, potassium or calcium hydroxide; bicarbonates, citrates and phosphates, etc.

One or both of the first or second fluids suitably comprise an active molecule or medicament. The active molecule, excipient or medicament may comprise any one or more of the pharmacologically active compounds from the group comprising:

- Peptides and proteins;
- H2-receptor antagonists such as cimetidine; and ranitidine;
- Prostaglandin analogues such as misoprostol;
- Proton pump inhibitors such as lansoprazole; omeprazole; and pantoprazole;
- Agents to treat food allergies such as sodium cromoglicate;
- Cardiac glycosides such as digoxin;

- Diuretics such as amiloride; bendroflumethiazide; indapamide; furosemide; hydrochlorothiazide; and xipamide;
- Drugs for arrythmias such as procainamide; lidocaine; propranolol; atenolol; bisoprolol; carvedilol; pindolol; and nebivolol;
- Antihypertensives and agents for treatment of angina such as clizapril; lisinopril; ramipril; trandolapril; amlodipine losartan; glyceryl trinitrate, isosorbide mononitrate; amlodipine; diltiazem; felodipine; isradipine; lacidipine etc.;
- Lipid regulating drugs such as statins;
- Drugs acting on the respiratory system such as salbutamol; terbutaline; bambuterol;
- Antihistamines such as cinnarizine; promethazine; perphenazine and prochlorperazine;
- Hypnotics such as zolpidem; zopiclone; clomethiazole;
- Anxiolytics such as benzodiazapines; buspirone;
- Antipsychotic agents such as benperidol; fluphenazine; pimozide and amisulpride;
- Antidepressant drugs such as tricyclics; mianserin; monoamine oxidase inhibitors (MAOIs); serotonin reuptake inhibitors (SRIs); reboxetine etc.;
- Central nervous system (CNS) stimulants such as methylphenidate;
- Drugs used in the treatment of nausea such as antihistamines; domperidone; metoclopramide; serotonin receptor (5HT3) antagonists; hyoscine, and betahistine;
- Opioid analgesics such as morphine; buprenorphine and fentanyl;
- Anti-migraine drugs such as serotonin receptor (5HT1) agonist and ergot alkaloids;
- Drugs used in treatment of Parkinsonism such as apomorphine; bromocriptine; lisuride; haloperidol and ergot alkaloids;
- Drugs used in substance dependence such as nicotine and buprenorphine;
- Drugs used in dementia such as rivastigmine; dihydroergotamine; dihydroergocristine and dihydroergokryptine;
- Antibiotics; antifungals; antivirals and antimalarials;
- Drugs used in treatment of diabetes;
- Glucocorticoid therapy using steroids such as betamethasone and dexamethasone;
- Male and/or female sex hormones such as estradiol; norethisterone; progesterone; testosterone and esters;
- Pituitary hormones such as vasopressin and desmopressin;
- Drugs affecting bone metabolism such as calcitonin and bisphosphonates;
- Endocrine drugs such as bromocriptine and cabergoline;
- Contraceptives such as oestrogens; progestogens and combinations thereof;
- Drugs used in urinary frequency and enuresis such as oxybutinin and desmopressin;
- Drugs used in erectile dysfunction such as apomorphine and sildenafil;
- Drugs used in malignant disease and immunosuppression such as busulfan; antimetabolites; alkaloids; corticosteroids; hormones and interferons;
- Non-steroidal anti-inflammatory drugs such as diclofenac; piroxicam and refoxicab;
- Drugs used in treatment of gout such as colchicines;
- Drugs used in neuromuscular disorders such as neostigmine and pyridostigmine;
- Muscle relaxants such as diazepam; tizanidine;
- Vaccines delivered by subcutaneous route;
- Agents for the treatment of nicotine withdrawal symptoms such as nicotine; and Cannabinoids.

At least one active compound may be a nutraceutically active compound. A "nutraceutically active compound" is a compound, derived from a natural origin (animal or vegetable) that has a beneficial and/or therapeutic effect on the human or animal body in the treatment of a condition. Such compounds may be regarded as nutrients.

Suitable nutraceutically active compounds may be natural products extracted from animals or vegetables. Examples of suitable nutraceutically active compounds include:

- Carotenoids such as lycopene, lutein, astaxanthin and □-carotene; glucosamine or Nacylglucosamine; ubiquinone;
- Vitamins such as vitamins A, C, D and E; Rosmarinic acid; Honokiol; Magnolol; Chlorogenic acid; Oleuropein; Methylsulphonylmethane ("MSM"); Collagen and Chondroitin; Boswellin and boswellic acid; Escin and esculin; Tumeric extracts such as curcuminoids and etrahydrocurcuminoids; Gingerol and gingerone; Triterpenes such as ursolic acid and oleanolic acid; Diterpenes such as asiaticoside, sericoside and ruscogenins; Hydroxycitric acid ("HCA") and niacinamide hydroxycitrate; Trigonellin; and Corosolic acid; Saw palmetto; and St John's Wort.

The device suitably comprises a battery, such as a disposable or rechargeable battery, for powering the heater of the first chamber and/or control circuitry.

The heater is suitably switched on or off using a switch. The switch is suitably an automatic switch that is triggered by the user inhaling on the device. The switch may therefore comprise a pressure-activated switch associated with the outlet of the device, whereby when a user draws on the device, the switch is turned on thereby automatically switching on the heater, and whereby the heater is switched off again when the user ceases drawing on the device. Suitably, the device additionally comprises a second pressure-sensitive switch for monitoring the pressure of the ambient air.

The second main chamber of the pulmonary delivery device containing the second fluid may also be breath-activated.

Another aspect of the invention provides a mouthpiece for a pulmonary delivery apparatus, the mouthpiece having a first inlet end and a second outlet end and comprising: a first mouthpiece chamber adapted for receipt within a main body of a pulmonary delivery device at the inlet end of the mouthpiece and a second mouthpiece chamber preferably concentrically surrounding the first chamber, the second chamber being adapted for receipt of at least one flavour or aroma and having at least one air inlet at the inlet end whereby the second chamber is selectively or continuously in fluid communication with air.

It is to be appreciated that the mouthpiece could be permanently attached to a pulmonary delivery device, for example forming part of the device but more preferably, the mouthpiece is a separate component.

The first and second mouthpiece chambers are preferably provided by concentric cylindrical walls. Preferably, the first chamber of the mouthpiece extends beyond the end of the second mouthpiece chamber at the inlet end. The outlet ends of the chambers are preferably substantially co-terminus. Preferably, the inlet end of the second chamber is provided with an annular flange extending substantially perpendicularly from the second chamber, the flange having at least one air inlet in fluid communication with the second chamber. A portion of the first chamber extends beyond the flange for receipt within a main body of a pulmonary delivery device and the flange is adapted to rest or engage with the sides of the main body, whereby the air inlets of the second chamber are positioned beyond the sides of the main body. Preferably, multiple air inlets are provided at the inlet end of the second chamber, preferably being spaced equidistant apart around the perimeter of the second chamber. Preferably, the air inlets are adjacent the portion of the first chamber that extends beyond the flange.

A flavour block is preferably provided within the second mouthpiece chamber.

In an alternative embodiment, the annular flange forms part of the inner mouthpiece chamber, the flange being provided with a series of holes for forming air inlets into the second mouthpiece chamber surrounding the first chamber.

The mouthpiece preferably includes means for selectively opening and closing the air inlets to the second chamber thereby enabling the volume of air entering the second chamber to be adjusted. For example, the second chamber may be at least partially rotatable with respect to the first chamber to open and close the air inlets, or vice versa. The walls of the cylinder forming the second chamber may be provided with spaced apart protuberances or tabs that can extend over and close the air inlets depending upon the degree of rotation of the second cylinder with respect of the first chamber. However, it is to be appreciated that other means may be provided to allow opening and closing of a desired selection of the air inlets.

In another embodiment, the second chamber is provided with multiple flavour blocks and the air inlets may be opened to allow flavour from only the desired flavour of the block. For example, the flavour block may comprise two half sections, each being of a different flavour, and the mouthpiece is provided with means for opening only the air inlets adjacent one of the half sections, for example, by the provision of a rotatable or slidable shutter. In another example, the flavours may be provided in inner and outer concentric rings within the second chamber and the air inlets are provided in corresponding inner and outer concentric rings, wherein the mouthpiece is provided with means for selective opening and closing of the inner or outer concentric rings.

BRIEF DESCRIPTION OF THE DRAWINGS

Embodiments of the invention shall now be described, by way of example only, with reference to the accompanying drawings in which.

DETAILED DESCRIPTION

Figure 1:
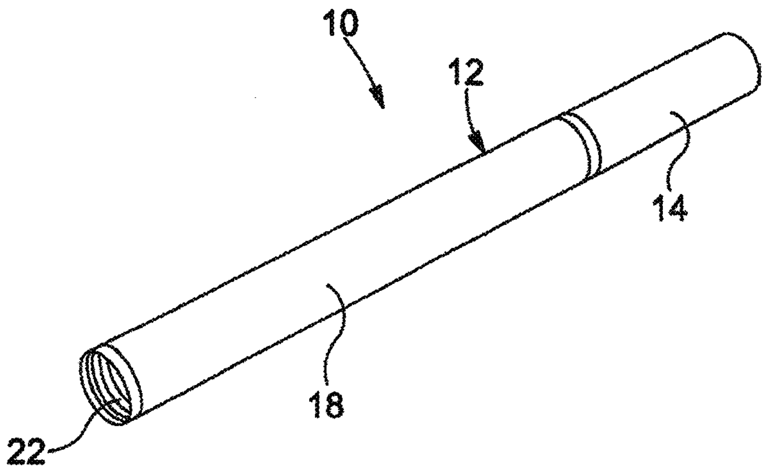
Figure 1 Prior Art
FIG. 1 is a perspective view of a pulmonary delivery device according to the prior art.

Referring to FIGS. 1, 2 and 3A to 3B of the accompanying drawings, a prior art pulmonary delivery device 10 comprises a generally cylindrical main body portion 12 adapted to resemble a cigarette. The main body portion 12 comprises a tubular filter chamber 14 encasing first and second vaporiser chambers 15, 16 and a tubular battery chamber 18 encasing a rechargeable battery 20. The tip 22 of the main body 12 is closed off by a translucent end cap 24, behind which sits an (light emitting diode (LED) indicator light 26 that illuminates when the device 10 is in use. A control circuit 28 is contained within the body 12, which comprises a programmable circuit for controlling the operation of the device 10, in use.

Figure 2:
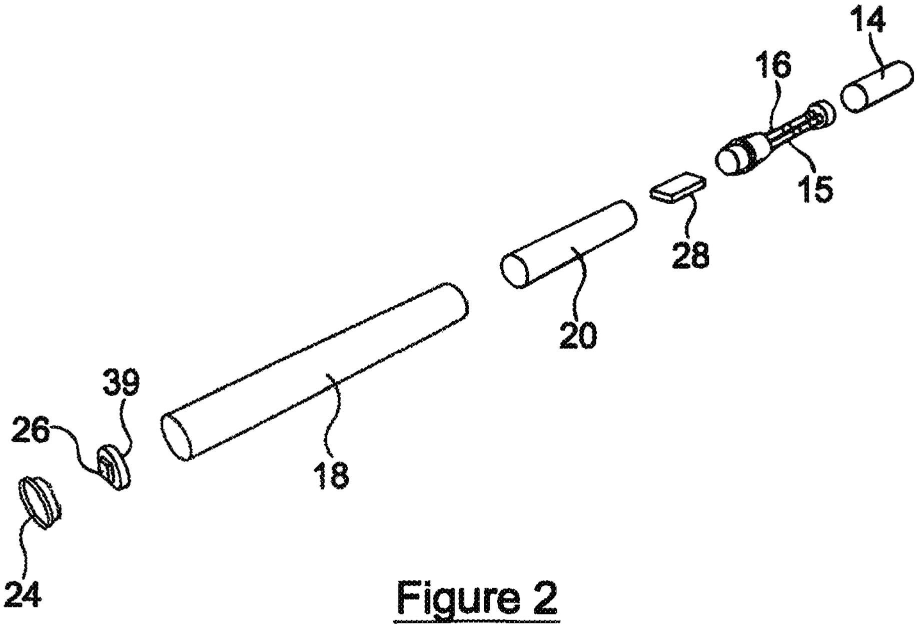
Figure 2 Prior Art
FIG. 2 is an exploded view of the pulmonary delivery device of FIG. 1.
Figure 3A:
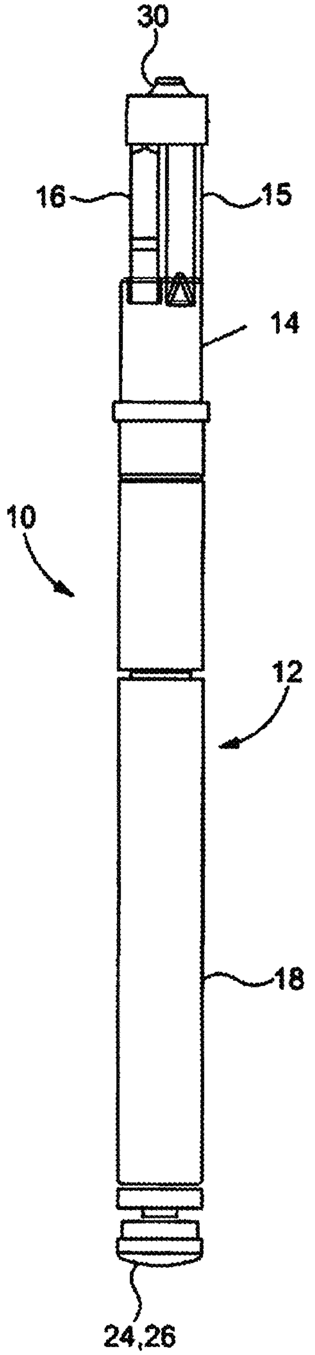
Figure 3A Prior Art
FIG. 3A is a plan view of the pulmonary delivery device of FIG. 1.
Figure 3B:
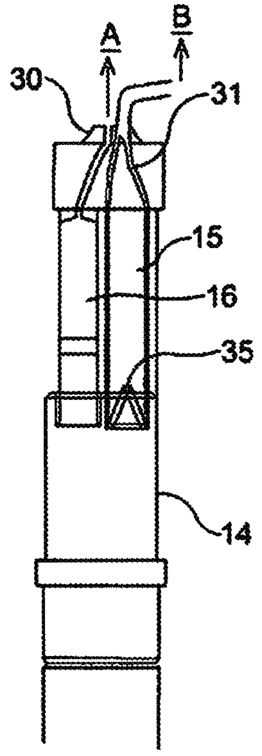
Figure 3B Prior Art
FIG. 3B is a close up view of part of FIG. 3A.

Turning to FIGS. 2 and 3, the device 10 comprises a first pressure sensor (not visible) located within the filter chamber 14, which has an outlet 30 therein through which, in use, vapour generated by the device 10 can be inhaled by a user. When the user draws on the filter chamber 14, the pressure sensor (not visible) activates the first and/or second vaporiser chambers 15, 16 to form a mixed vapour comprising the first and/or second liquids, to be inhaled.

The first and second vaporiser chambers 15, 16 comprise a pair of separate reservoirs containing first and second liquids respectively. A first vaporiser chamber 15 contains a first liquid and comprises a capillary wick 31, which absorbs the liquid, and whose end touches a heater element 35 in the form of a pyramid-shaped, super-hydrophilic foil, which is wetted by the first liquid, in use (see, in particular, FIG. 3B). The heater element 35 could alternatively comprise a resistive heating coil, which is wrapped around the wick 31. In any event, the heater element 35 is connected to the battery 20 under the control of the control circuit 28.

The second vaporiser chamber 16 contains a second liquid that is held under pressure within the chamber and includes a pressure release valve or flow control valve (not shown). When the user draws on the filter chamber, the pressure sensor activates the valve to propel the second liquid out of the second chamber as a fine mist or vapour. The absence of any heating element results in a cold vapour being released from the second chamber.

Thus, when the heater element 35 is switched on, the first vaporiser chamber acts as a "warm vapour chamber" with the first liquid being evaporated and forming a warm vapour B within the interior of the filter chamber 14. Simultaneously, cold vapour A is released into the interior of the filter chamber 14 from the second vaporiser chamber (the "cold vapour chamber") thus allowing the warm and cold vapours B, A to mix in the hollow space of the filter chamber, before being inhaled by the user, via the outlet 30 of the device.

The first liquid comprises a mixture of glycerol and water and the second liquid comprises nicotine and a suitable propellant. Preferably, the particles forming the mist of the second liquid are less than 10 μm in diameter, more preferably less than 5 μm. In this manner, nicotine (or other active molecule provided in the second liquid) is delivered deep into the lungs to allow for its quick absorption into the bloodstream via the lungs. However, the simultaneous delivery of a warm, wet vapour in the form of the vaporised first liquid provides the user with a sensation that more closely resembles that experienced during the smoking of a conventional tobacco cigarette. The active molecule is not in direct contact with the heater element, reducing the potential for its thermal degradation which may have resulted in the user inhaling harmful by-products. In contrast, only glycerol and water are in contact with the heater element which do not result in the production of harmful by-products upon their thermal degradation.

The device may also be provided with a suitable control circuit 28 that may control the delivery of the first and/or second vapours from their respective chambers. The ability to deliver nicotine from a pressurized chamber without heating allows for more accurate nicotine dosing using the device of the present invention than the delivery of nicotine using the heated vapour method. It is to be appreciated that the delivery of the wet warm vapour and the cold vapour may be controlled and the content of the mixed vapour may be adjusted as required.

For example, the control of the delivery of heated vapour may be achieved using a resistance sensor operatively connected to the heater element 35 which measures the heater's resistance, and infers from that, the heater temperature. The control circuit 28 additionally comprises a current limiting circuit for limiting the current to the heater element 35 and is programmed to heat it according to a predetermined, time-dependent heating/cooling profile.

When a user draws on the filter chamber 14, the pressure switch (not visible) triggers the control circuit 28 to heat the heater element 35. The control circuit 28 thereby connects the battery 20 to the heater element 35 in a controlled and reproducible manner. As such, the time, and time-at-temperature of the heater element 35 is thus controlled, thereby regulating the vaporisation of the first liquid from the wick 31.

The control circuit 28 may also be operatively connected to a second pressure sensor 39 (FIG. 2), which measures the ambient air pressure. The control circuit 28 is configured to switch on the heater element 35 only when the first pressure switch is triggered, as described hereinabove.

A vapour is thereby formed adjacent the heater element within a hollow interior space (a mixing chamber) located towards the tip of the filter chamber 14, i.e. the space between the first vaporiser chamber 15 and the outlet 30, when the device 10 is assembled.

The outlet from the "cold vapour chamber" or second vaporiser chamber is sufficiently small as to control (mass-limit) the amount of the second liquid that can escape in each dispensation, and is selectively closed and/or opened by a control valve (not shown). The control valve is connected to the control circuit 28 enabling it to be controlled independently of the heater element. The control circuit 28 can thus be configured to open the valve a given number of times, per actuation, thereby incrementally controlling the dose of liquid dispensed (the dose per actuation being constant due to the size of the outlet aperture). Thus, the device is able to accurately control the ratio of the first and second liquids dispensed in each actuation, and hence the dose of a particular medicament or mixture of medicaments in the first and second liquids. The ratio may be adjusted by the control circuit 28, in accordance with a pre-programmed dosing regimen.

While the afore-mentioned device may accurately control the dose provided by each chamber, if the active molecule or medicament is only included in the "cold vapour" chamber then it is possible to only accurately control dosing provided by this chamber. This allows for simpler control of dosing than when the active molecule or medicament is dispensed in the warm vapour.

Figure 4:
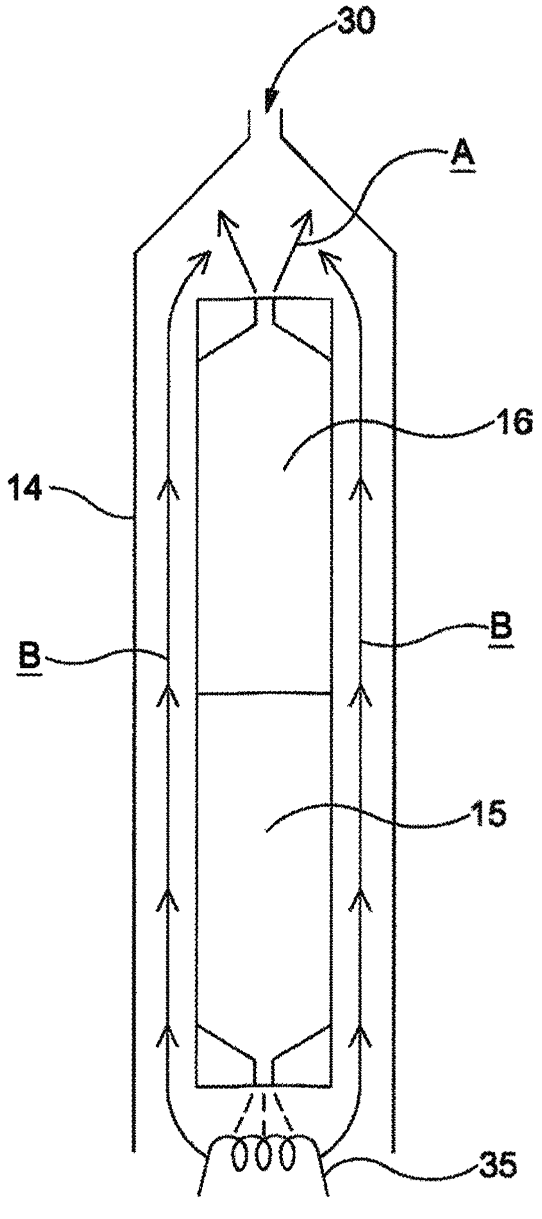
Figure 4 Prior Art
FIG. 4 is a plan view of another pulmonary delivery device that forms part of the state of the art.

FIG. 4 shows an alternative pulmonary delivery device forming part of the state of the art. In FIG. 4, the first and second vaporiser chambers are not in a side-by-side arrangement but instead arranged along the longitudinal axis of the device, in an end-to-end arrangement, thereby providing a slim-line device.

Features that are identical to those described in FIGS. 1 to 3 are given the same reference numerals, for the sake of simplicity. The first and second vaporiser chambers 15, 16 are provided in a hollow cylindrical pressure vessel comprising a dual ended aerosol container having an aerosol outlet at each end, the container being surrounded by housing having outlet 30. The second vapour chamber 16 is provided in the intended top end of the aerosol container near to the outlet 30 and the first vapour chamber 15 extends from the base of the chamber 16 in the bottom end of the aerosol container. A heating element 35 is provided in line with the base of the aerosol container. The second liquid containing the active molecule is dispensed from the upper chamber (as cold vapour designated by reference character A) and the first liquid is dispensed from the lower chamber on to the heating element 35 (warm vapour designated by reference character B). This warms up the second vapour which then passes up the passage (warm vapour B) between the housing and container to the outlet 30, thereby enabling mixing of the hot and cold vapours (B, A) prior to their exit through the outlet and inhalation by the user.

In this example, the control circuit may be programmed to activate vapourisation of the first liquid in the warm vapour chamber a few milliseconds before release of vapour from the cold vapour chamber thereby ensuring that warm vapour is released simultaneously with the cold vapour.

It is to be appreciated that alternative arrangements may be provided for the warm and cold vaporiser chambers in the device. For example, the device may include a dual chamber having a hollow cylindrical pressure vessel comprising a central divider thus dividing the interior thereof into two separate reservoirs for first and second liquids. A pressurised propellant gas occupies the remaining space of one reservoir and a heater element and wick is provided in the other reservoir, with outlet apertures provided to enable the liquids to escape from their respective reservoirs under the actions of the pressurised propellant and heater element.

A ceramic heater may be used for heating the first liquid in the first chamber. This reduces the potential for harmful metal residues from metallic heating elements to be inhaled by the user.

An alternative type of "cold vapour" chamber may comprise a spring-loaded syringe comprising a tubular body portion forming a reservoir for retaining the second liquid. A piston is slideably moveable within the body and is sealed thereto by an O-ring seal. A superelastic spring cooperates between the rear face of the piston and an end cap of the body to push the piston along the body and thus eject the liquid contained therein through an outlet aperture. An outlet flow control valve is also provided to open and close the outlet aperture. The super elastic spring is compressed within its super elastic range and, provided the superelastic spring is operated within this range, the pressure of the liquid remains constant, thereby accurately regulating the amount of liquid dispended during each actuation of the valve.

A device incorporating this type of "cold vapour" vaporiser would, of course, also include a "warm vapour" chamber with a heating element for releasing a warm vapour, and, optionally, a control circuit 28 to control the delivery of the liquids.

Figure 5:
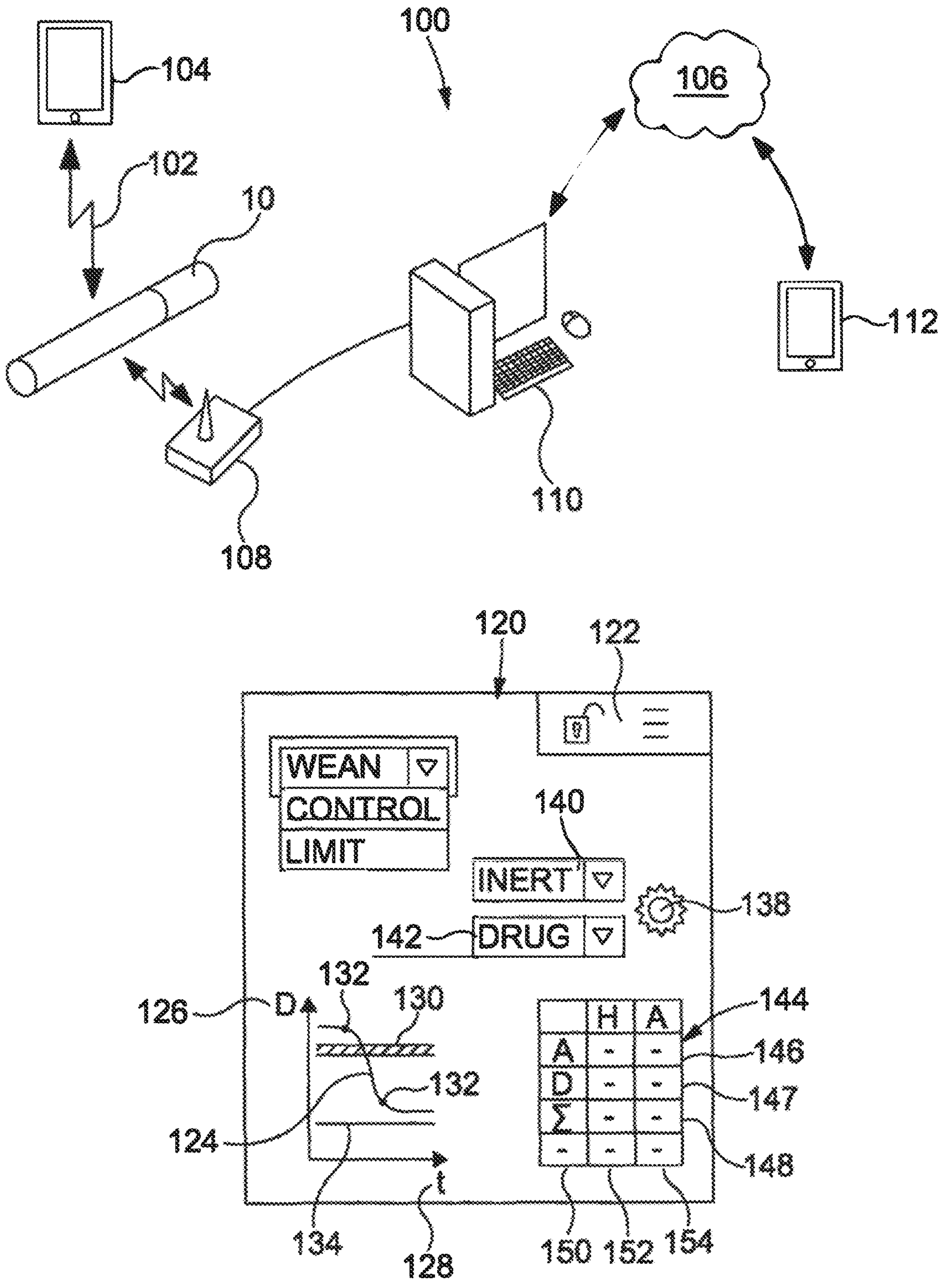
FIG. 5 is a schematic view of a pulmonary delivery device and user interface.
Figure 6A:
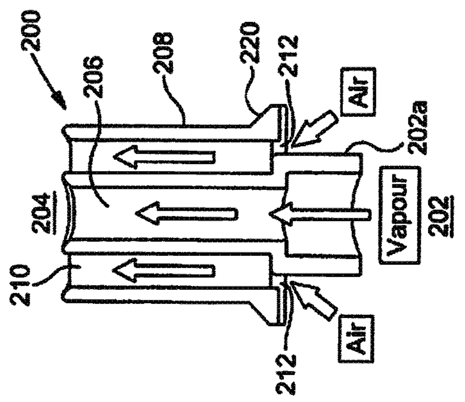
FIG. 6A is a cross-section through a mouthpiece according to an embodiment of the present invention for attachment to a pulmonary delivery device.
Figure 6B:
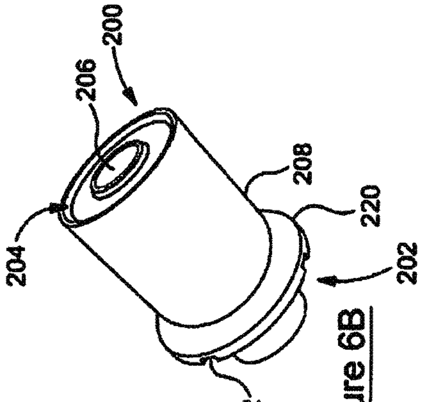
FIG. 6B is a perspective view of the mouthpiece shown in FIG. 6A with a flavour block fully inserted into the second chamber.
Figure 6C:
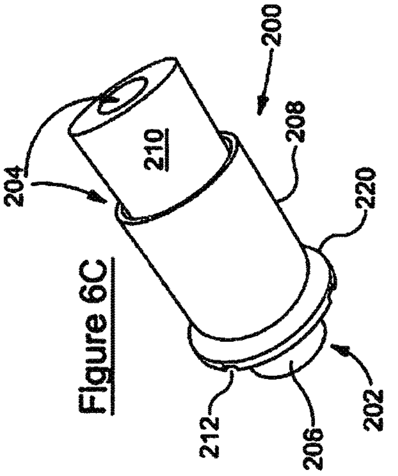
FIG. 6C is a perspective view of the mouthpiece shown in FIG. 6A with a flavour block partially inserted into the second chamber.
Figure 6D:
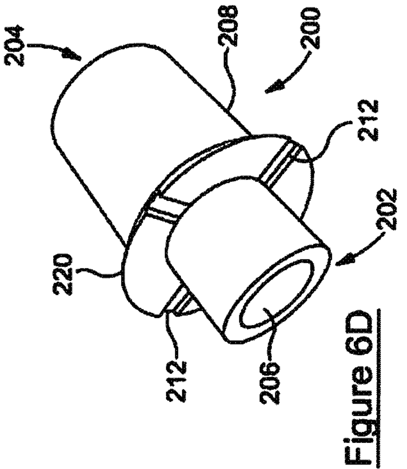
FIG. 6D is a perspective view of the mouthpiece of FIG. 6A illustrating the air inlets of the second chamber.

A dose control system 100 is shown in FIG. 5 of the drawings. In FIG. 5, a pulmonary delivery device 10 such as that shown in in FIGS. 1 to 3B, FIG. 4 or FIGS. 6A to 7 is wirelessly connected 102 to a user's smartphone, tablet computer or PC 104 and to the internet 106, via a Wi-Fi access point 108, such as a broadband router. Internet connected computers 110, 112 (local or remote) can thus connect to the device 10 wirelessly, as can the user him or herself. The wireless connection is provided via a Wi-Fi and/or Bluetooth® interface of the control circuit 28, thereby providing a graphical user interface (GUI) 120 on any of the devices 104, 110, 112 for interacting with the device 10.

The GUI 120 has a secure login-in system 122 to prevent unauthorised re-configuration of the device 10 and allows a user to select between three main modes of operation, namely a "wean" mode 124 whereby the dose 126 of a given medicament can be reduced over time 128, as shown on a dose-time graph 130 of the GUI. The graph has draggable handles 132 that enable the shape of the curve to be adjusted to change the weaning profile, i.e. the severity, duration, delay etc. of the weaning process.

Another option from the drop-down menu is to select a control program 134, which ensures that a desired quantity of medicament is administered over a period of time. The dose-per-puff is thus controlled to ensure, on average, a relatively even administration of the medicament over the time period.

A third option is to set an upper limit, which may be useful in analgesic applications. This program prevents a maximum dose per unit time from being delivered, but allows for under-administration.

The GUI 120 comprises a configuration settings menu 138, which enables a user to configure the GUI in accordance with the liquids 140, 142 in the device. A history table 144 is also provided, which provides a summary of the number of administrations 146, the amount of medicament delivered 147 and a running total 148. These data are shown on a historic 150, actual 152 and a target 154 basis to facilitate monitoring of the drug delivery to the user.

The device is not restricted to the details of the foregoing examples. For example, the shape and configuration of the device can be changed, the materials of manufacture, the combinations of vaporiser technology used, the combinations of heaters used, the additional features, such as the on/off switch, control valves etc. can be varied.

For example, the first "warm vapour" chamber containing an inert liquid, such as a water-glycol mixture, which forms an inhalable vapour may be consumed without restriction by a user. The device has a pressure switch located within the filter chamber 14, which detects when a user inhales on the device. The pressure switch is connected to the control circuit 28, and the control circuit is adapted to switch on a current, from the battery 20, to a resistive heating coil wrapped around an end of the wick, which evaporates the first liquid to form a vapour that can be drawn from the device, via the vaporiser outlet and the device's outlet 30.

The device may additionally comprise a push switch that is accessible from the exterior of the device, which a user can depress, in use, to actuate the valve of the "cold vapour" second vaporiser chamber. Thus, a user can use the device at will, and can choose when to administer a dose of a medicament or active ingredient, such as nicotine, which is contained in the second chamber, by pressing on the button during inhalation.

The afore-mentioned device provides many potential advantages over earlier pulmonary delivery devices. The active ingredient, such as nicotine or a cannabinoid, is inhaled as small particles (<10 μm) resulting in it being delivered deep into the lungs of a user enabling its fast absorption into the bloodstream. The simultaneous delivery of a warm inert vapour enhances the flavour and sensation of the inhalation. The active ingredient is not subject to thermal degradation, leading to a reduction in any harmful by-products and increasing the accuracy and reproducibility of the dosage.

A device according to embodiments of the present invention is illustrated in FIGS. 6A-6D, FIG. 7 and FIGS. 8A to 8C of the accompanying drawings. The device is an adaptation of the devices hereinbefore described and addresses the problems associated with flavourings, such as oils, being delivered in a hot wet vapour and the contamination of a pulmonary delivery device by said flavourings.

The invention overcomes significant regulatory burden of inhalation toxicology for various flavour compounds where inhalation data is not known or where the risk of inhalation is significantly greater than oral deposition.

The invention provides delivery of the flavor or aroma in a "cold" atomized vapour. This is in contrast to the devices of the prior art that deliver the flavor or aroma with the carrier liquid (such as water, or a water-glycol mixture) from a heated chamber. Thus, in the pulmonary delivery device shown in FIGS. 1 and 4 the aroma or flavour would be provided in the second chamber, optionally with the active molecule, rather than the first chamber that provides a relatively warm vapour relative to the second chamber. This ensures that the flavour is delivered to the mouth and prevents degradation of the flavour to harmful by-products that may occur on heating.

The provision of flavours in the warm vapour according to the prior art also causes contamination or carryover in the tank/chamber system of the device. An embodiment of the present invention enables the flavour of an electronic nicotine delivery system (ENDS) to be changed without contamination or carryover in to the tank system. Coffee, tobacco, mint and fruit flavours are often difficult to alternate due to their characteristic aromas. The invention as described in FIGS. 6A to 6D, 7 and 8A to 8C enables the use of a flavour block in the aerosolising chamber to reduce or eliminate cross-contamination of flavour from use to use with simple changeover. Currently the flavours are integral part of the propylene glycol/water in devices available.

Figure 7:
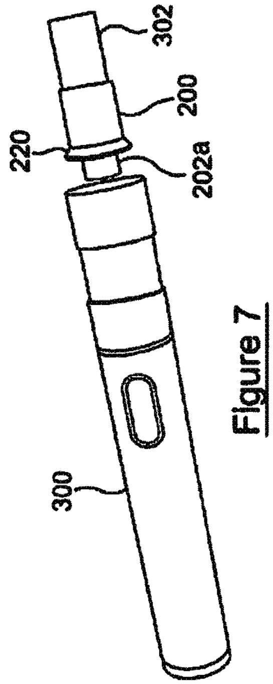
FIG. 7 is perspective view of a prior art pulmonary delivery device and mouthpiece according to the present invention.
Figure 6E:
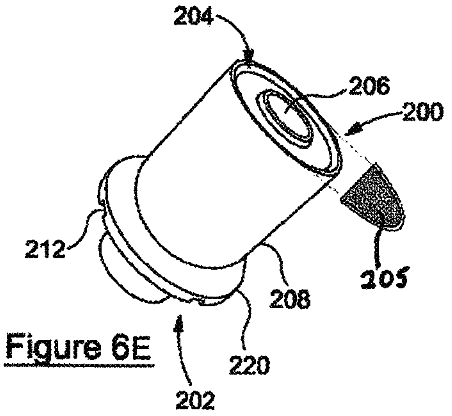
FIG. 6E is a partially exploded perspective view of an alternate embodiment of the mouthpiece of FIG. 6A having a slidable shutter.

The embodiment shown in FIGS. 6A to 6D is a mouthpiece 200 for attachment to a conventional pulmonary delivery device, such as a pulmonary delivery device 300 shown in FIG. 7. The mouthpiece has an inlet end 202 and an outlet end 204 with a first central chamber 206 consisting of a cylindrical tube which is adapted for receipt within a main body of the pulmonary delivery device 300 at the inlet end 202 of the mouthpiece. A second chamber 208 concentrically surrounds the first chamber, the second chamber being adapted for receipt of at least one flavour block 210 and having at least one air inlet 212 at the inlet end.

The first central chamber 206 of the mouthpiece extends beyond the inlet end of the second chamber. The outlet ends 204 of the chambers are substantially co-terminus. The inlet end of the second chamber is provided with an annular flange 220 extending perpendicularly from the second chamber, the flange having the at least one air inlet 212 in fluid communication with the second chamber. A portion 202*a* of the first chamber extends beyond the flange for receipt within a main body of a pulmonary delivery device and the flange is adapted to rest or engage with the sides of the main body, whereby the air inlets of the second chamber are positioned beyond the sides of the main body. A filter tip 302 may also be received at the outlet end 204 of the mouthpiece (see FIG. 7).

It is to be appreciated that multiple air inlets 212 may be provided at the inlet end of the second chamber, preferably being spaced equidistant apart around the perimeter of the second chamber to optimize air flow into the second chamber. Ideally, the air inlets 212 lie adjacent the portion of the first chamber that extends beyond the flange.

Any desired flavour block 210 may be provided within the second chamber 208. In this manner, when the mouthpiece 200 is attached to the pulmonary delivery device and a user inhales with the mouthpiece, warm wet vapour from the main body of the device enters the first chamber 206 of the mouthpiece. Simultaneously, air is able to enter the second chamber through air inlets 212 to atomise the flavour in the flavour block. This results in the user having a mixture of warm wet vapour with a cold vapour that contains the flavour, addressing the cold sensation of delivery of some nicotine products or other active agents without the potential of harmful ingredients of flavourings being orally deposited.

This arrangement is not only less detrimental to health because the flavouring, such as an oil, is not subjected to heat, but also enables the mouthpiece to be easily changed for a mouthpiece having a different flavor block, without any contamination of the main pulmonary delivery device.

Ideally, but not essentially, the nicotine or other active agent is also delivered via the cold chamber. Combination of this unheated gas with a heated aerosol (typically flavourless) is thought to increase customer satisfaction and is likely to result in a product more akin to customer expectations of a nicotine-containing product.

The embodiment shown in FIGS. 6A to 6D and 7 is preferably formed from a simple two piece construction. The mouthpiece may be disposed of after use and replaced with a new mouthpiece or may have the flavor block removed, be cleaned and a new flavor block inserted. Thus, this provides an easy mechanism for a user to change the flavor or their device, for example from cherry to menthol.

Figure 8C:
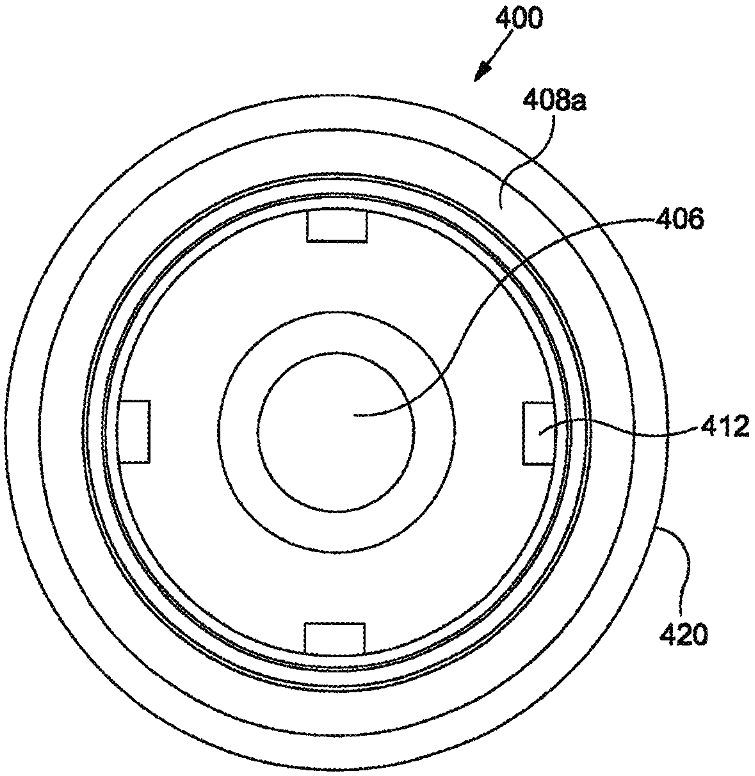
FIGS. 8A, 8B and 8C are respectively a perspective view, a partial cross-sectional view and a top view of a mouthpiece according to another embodiment of the present invention for attachment to a pulmonary delivery device.
Figure 8D:
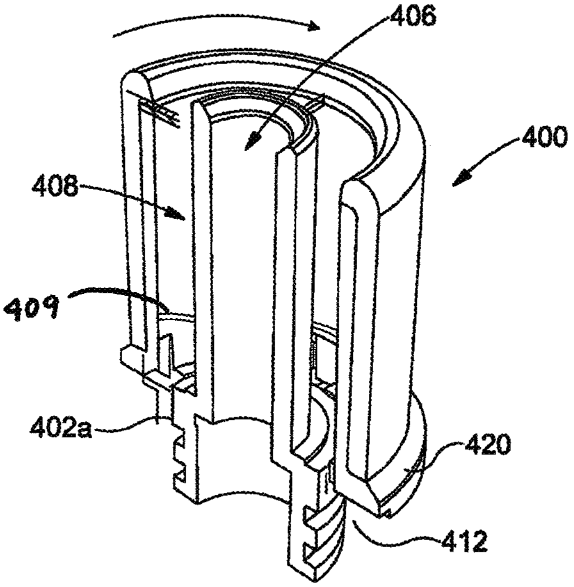
FIG. 8D is a perspective view of an alternate embodiment of the mouthpiece of FIG. 8B.
Figure 8A:
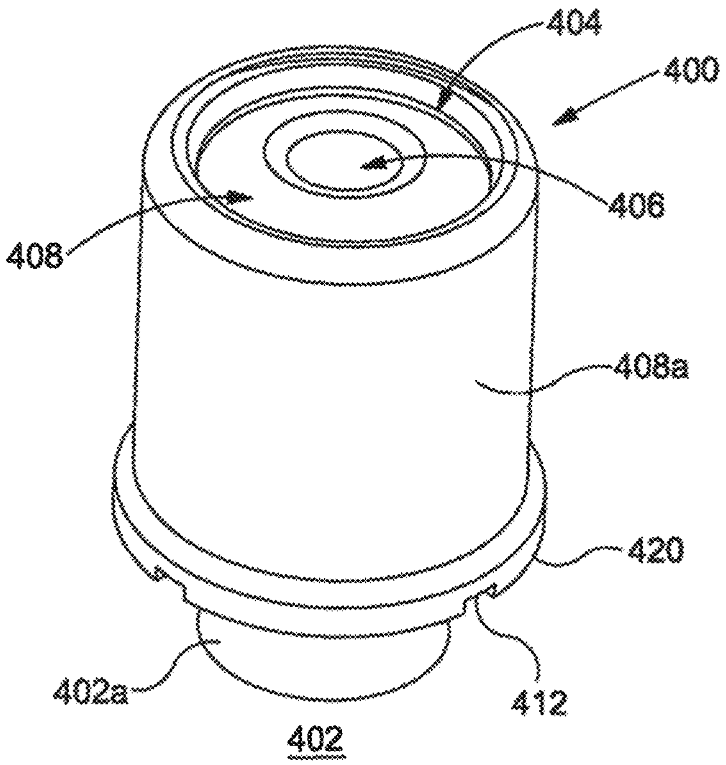
Figure 8B:
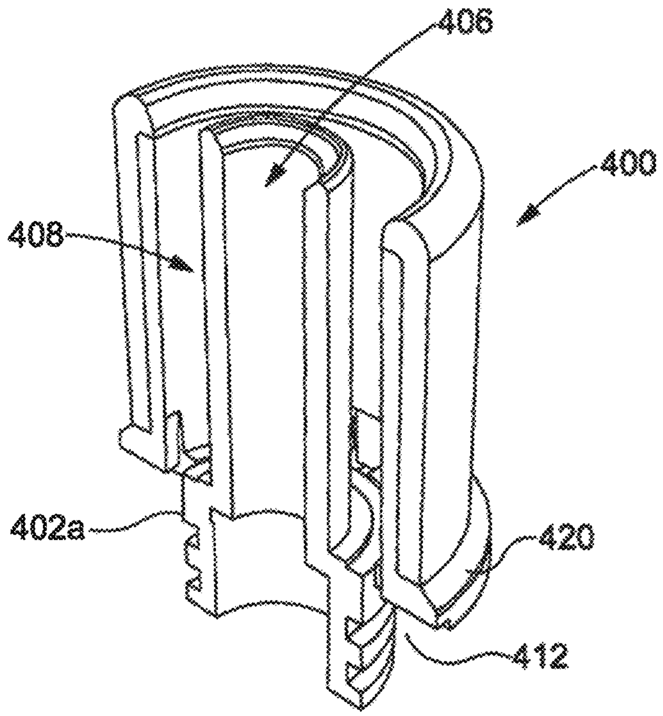

Another embodiment of a mouthpiece according to the present invention is shown in FIGS. 8A to 8A. The mouthpiece 400 is similar to mouthpiece shown in FIGS. 6A to 6D having outlet end 404 and inlet end 402 but the annular flange 420 is formed as part of the moulding forming the first mouthpiece chamber 406 and a cylindrical sleeve 408*a* rests on the flange to form the second chamber 408. Air inlets 412 are provided through the flange and the portion of the first mouthpiece chamber 402*a* that extends beyond the inlet end 402 of the second chamber is threaded for engagement with the heated chamber of a pulmonary delivery device (not shown). The sleeve is preferably of a more malleable material than the rest of the mouthpiece to increase user comfort.

In a preferred embodiment of the present invention, the number of air inlets that are open to the second chamber are selectively adjustable to vary the flow of air through this chamber. This enables a user to select the amount of flavour that is inhaled and mixed with the hot vapour. Alternatively, or additionally, more than one type of flavour may be provided in the second chamber with the user being able to select which air inlets to open dependent upon which flavour is to be inhaled.

For example, the mouthpiece may have means for opening and closing the air inlets to the second chamber thereby enabling the volume of air entering the second chamber to be adjusted (not shown). For example, the second chamber may be at least partially rotatable (see arrow of FIG. 8D) with respect to the first chamber to open and close the air inlets or vice versa. The walls of the cylinder forming the second chamber may be provided with spaced apart protuberances or tabs 409 (see FIG. 8D) that can extend over and close the air inlets depending upon the degree of rotation of the second cylinder with respect of the first chamber.

In another embodiment, the second chamber is provided with multiple flavour blocks and the air inlets may be opened to allow flavour from only the desired flavour of the block. For example, the flavour block may comprise two half sections, each being of a different flavour, and the mouthpiece is provided with means for opening only the air inlets adjacent one of the half sections, such as by the provision of a rotatable or slidable shutter 205 (e.g., FIG. 6E). In another example, the flavours may be provided in inner and outer concentric rings within the second chamber having air inlets provided in a corresponding arrangement of inner and outer concentric rings, wherein the mouthpiece is provided with means for selective opening and closing of the air inlets of inner or outer concentric rings. This would enable a user to easily select a particular flavour without having to change the mouthpiece. This is desirable as many users get used to a flavour very quickly and may wish to alternate flavours, such as cherry and mint, throughout the day.

The invention claimed is:

1. A pulmonary delivery device incorporating a mouthpiece, the device comprising:

a main body having a first chamber for receiving a first fluid, the first chamber having a heating element adapted to thermally vaporise a quantity of the first fluid to form a relatively warm, wet first vapour and an outlet, and the mouthpiece being connectable to the main body via the outlet, the mouthpiece comprising an inner part forming an extension to the first chamber of the main body for passage of the first vapour and having an outer part forming a second chamber adapted for receipt of at least one flavour or aroma, wherein the second chamber includes at least one air inlet selectively or continuously communicating with air to provide a passive atomizer to atomize a quantity of the flavour or aroma without heating, wherein the flavour or aroma is inhaled by drawing air through the at least one air inlet of the second chamber.

2. The pulmonary delivery device as claimed in claim 1, wherein the flavour is provided in a solid or semi-solid form within the second chamber.

3. The pulmonary delivery device as claimed in claim 1 wherein the inner part forming the extension of the mouthpiece is receivable within the main body of the device such that the mouthpiece is reversibly detachable to the main body of the device.

4. The pulmonary delivery device as claimed in claim 3, wherein the outer part of the mouthpiece forming the second chamber at least partially surrounds the inner part forming the extension to the first chamber.

5. The pulmonary delivery device as claimed in claim 4, wherein the inner part of the mouthpiece forming the extension to the first chamber comprises a central extension with the outer part forming a concentric outer second part surrounding the inner part to form the second chamber.

6. The pulmonary delivery device as claimed in claim 4, wherein the outer part forming the second chamber terminates in a flange having the at least one air inlet wherein the flange is received on a top surface of the main body of the pulmonary delivery device.

7. The pulmonary delivery device as claimed in claim 3, wherein an annular flange extends laterally from the inner part forming the extension of the mouthpiece, the flange having the at least one air inlet into the second chamber surrounding the inner part forming the extension to the first chamber.

8. The pulmonary delivery device as claimed in claim 3, wherein multiple air inlets are provided into the second chamber and entry of air through the air inlets is adjustable, wherein the number and/or size of the air inlets that are open into the second chamber is adjustable.

* * * * *